United States Patent
Onishi et al.

(10) Patent No.: US 8,652,448 B2
(45) Date of Patent: Feb. 18, 2014

(54) HYDROGEL PARTICLES

(75) Inventors: Yuka Onishi, Wakayama (JP);
Kimikazu Fukuda, Wakayama (JP);
Kazuo Matsuyama, Wakayama (JP);
Koji Mine, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/519,002

(22) PCT Filed: Dec. 16, 2010

(86) PCT No.: PCT/JP2010/007306
§ 371 (c)(1),
(2), (4) Date: Jun. 25, 2012

(87) PCT Pub. No.: WO2011/077674
PCT Pub. Date: Jun. 30, 2011

(65) Prior Publication Data
US 2012/0288457 A1    Nov. 15, 2012

(30) Foreign Application Priority Data

Dec. 24, 2009 (JP) ................................ 2009-293119

(51) Int. Cl.
*A61K 8/92* (2006.01)
*A61K 8/04* (2006.01)
*A61Q 17/04* (2006.01)

(52) U.S. Cl.
USPC ............................................. 424/60; 424/59

(58) Field of Classification Search
None
See application file for complete search history.

(56) References Cited

U.S. PATENT DOCUMENTS

| | | | |
|---|---|---|---|
| 6,391,288 B1 | 5/2002 | Miyazawa et al. | |
| 8,017,046 B2 | 9/2011 | Sakai et al. | |
| 2002/0034525 A1 | 3/2002 | Sakai et al. | |
| 2008/0220031 A1* | 9/2008 | Wunsch et al. | 424/401 |
| 2009/0155323 A1 | 6/2009 | Sakai et al. | |
| 2009/0163607 A1 | 6/2009 | Mine et al. | |
| 2010/0015186 A1 | 1/2010 | Takagi et al. | |
| 2010/0209463 A1* | 8/2010 | Pfluecker et al. | 424/401 |
| 2011/0236446 A1 | 9/2011 | Takagi et al. | |
| 2011/0268674 A1* | 11/2011 | Filbry et al. | 424/59 |

FOREIGN PATENT DOCUMENTS

| | | |
|---|---|---|
| CN | 1287877 A | 3/2001 |
| CN | 101330970 A | 12/2008 |
| EP | 1 172 083 | 1/2002 |
| EP | 1172083 * | 1/2002 |
| JP | 2001 96146 | 4/2001 |
| JP | 2002 20227 | 1/2002 |
| JP | 2002 37713 | 2/2002 |
| JP | 2002 159838 | 6/2002 |
| JP | 2003 238693 | 8/2003 |
| JP | 2003 252722 | 9/2003 |
| JP | 2004 107306 | 4/2004 |
| JP | 2007 153835 | 6/2007 |
| JP | 2007 160277 | 6/2007 |
| JP | 2008 19195 | 1/2008 |
| JP | 2008 303163 | 12/2008 |
| JP | 2010 275269 | 12/2010 |
| WO | 2010 061556 | 6/2010 |

OTHER PUBLICATIONS

English Translation of the International Preliminary Report on Patentability and Written Opinion issued Jun. 26, 2012 in PCT/JP2010/007306.
Combined Chinese Office Action and Search Report issued Feb. 25, 2013 in Patent Application No. 201080056838.2 with English Translation and English Translation of Category of Cited Documents.
Yamori, Y., "Formulation design by the organic conceptional diagram," Fragrance journal, vol. 17, No. 4, pp. 29-38 and 143, Apr. 1989 (with English abstract and computer generated translation).
Sakai, Y., "Property of emulsion used high polar oil and application to cosmetic," Fragance Journal extra edition, No. 19, pp. 76-82 and 156, Apr. 26, 2005 (with English abstract and computer generated translation).
Japanese Office Action Issued Apr. 24, 2012 in JP Patent Application No. 2010-280463 (with English translation).
International Search Report Issued Mar. 22, 2011 in PCT/JP10/07306 Filed Dec. 16, 2010.

* cited by examiner

*Primary Examiner* — Frederick Krass
*Assistant Examiner* — Celeste A Roney
(74) *Attorney, Agent, or Firm* — Oblon, Spivak, McClelland, Maier & Neustadt, L.L.P.

(57) ABSTRACT

Hydrogel particles include: a continuous phase of non-crosslinked hydrogel; and a dispersed phase dispersed in the continuous phase. The dispersed phase includes a crystalline organic UV absorber and a solid fat having an organic value (OV) of 310 or more and an inorganic value (IV) of 130 or more on an organic conceptual diagram. The content of the crystalline organic UV absorber in the dispersed phase is 15-70 mass %.

23 Claims, No Drawings

HYDROGEL PARTICLES

TECHNICAL FIELD

The present disclosure relates to hydrogel particles and methods for producing hydrogel particles.

BACKGROUND ART

Application of hydrogel particles including oil components has been examined in the fields of cosmetics, drugs, quasi drugs, and the like (see, for example, Patent Document 1). Patent Document 2 shows a skin cosmetic product in which hydrogel particles including an oil component are dispersed in an aqueous solvent.

CITATION LIST

Patent Document

[Patent Document 1] Japanese Patent Publication No. 2002-159838
[Patent Document 2] Japanese Patent Publication No. 2002-20227

SUMMARY OF THE INVENTION

The present disclosure is directed to hydrogel particles including: a continuous phase of non-crosslinked hydrogel; and a dispersed phase dispersed in the continuous phase, wherein the dispersed phase includes a crystalline organic UV absorber and a solid fat having an organic value of 310 or more and an inorganic value of 130 or more on an organic conceptual diagram, and a content of the crystalline organic UV absorber in the dispersed phase is 15-70 mass %.

The present disclosure is also directed to a method for producing hydrogel particles in which a dispersed phase including a crystalline organic UV absorber and a solid fat having an organic value of 310 or more and an inorganic value of 130 or more on an organic conceptual diagram is dispersed in a continuous phase of non-crosslinked hydrogel including a gel-forming agent and water, by dropping, spraying, or stirring a mixture including the crystalline organic UV absorber, the solid fat, the gel-forming agent, and the water, wherein the mixture is prepared such that a content of the crystalline organic UV absorber in the dispersed phase in the hydrogel particles is 15-70 mass %.

The present disclosure is also directed to an UV-shielding cosmetic product containing the hydrogel particles of the present disclosure.

DESCRIPTION OF EMBODIMENTS

An embodiment will be described in detail hereinafter.

Hydrogel Particles

Hydrogel particles according to this embodiment are to be included in, for example, cosmetics, drugs, quasi drugs, and include a continuous phase of non-crosslinked hydrogel and a dispersed phase dispersed in the continuous phase. The dispersed phase includes a crystalline organic ultraviolet radiation (UV) absorber and a solid fat having an organic value (OV) of 310 or more and an inorganic value (IV) of 130 or more on an organic conceptual diagram. The content of the crystalline organic UV absorber in the dispersed phase is 15-70 mass %.

The crystalline organic UV absorber is included in, for example, cosmetics, but has low solubility in various types of oils and solvents commonly used in cosmetics. Thus, it is difficult to incorporate the crystalline organic UV absorber in cosmetics with stability.

Incorporating the crystalline organic UV absorber in the hydrogel particles has problems such as a low degree of flexibility in prescription and deterioration of UV absorption ability for the following reasons. For example, the crystalline organic UV absorber is not easily dissolved in oil components. In addition, when the crystalline organic UV absorber is dissolved in an oil component, crystal is easily precipitated in a solution in a storage period.

With the hydrogel particles of this embodiment, however, the foregoing composition can reduce crystal precipitation of the crystalline organic UV absorber in a storage period regardless of a high concentration of 15-70 mass % of the crystalline organic UV absorber in the dispersed phase.

The "hydrogel particles" herein means one or a plurality of particles in which a dispersed phase is dispersed in a continuous phase of non-crosslinked hydrogel, excluding a capsule composed of an inner layer, i.e., a core, and an outer layer, i.e., a shell, which are concentrically disposed. The "hydrogel" herein is a gel obtained from a gel-forming agent using water as a solvent. The structure in which the dispersed phase is dispersed in the continuous phase in the hydrogel particles can be observed by, for example, photography analysis with a freeze-fracture SEM.

From the viewpoints of appearance and productivity, the volume-based average particle size of the hydrogel particles is preferably 10-10000 μm, more preferably 10-5000 μm, much more preferably 30-3000 μm, still much more preferably 60-500 μm, and especially preferably 60-250 μm. The volume-based average particle size of the hydrogel particles can be measured with a laser diffraction/scattering method (e.g., LA-920 manufactured by HORIBA, Ltd.) or a sieve method. To measure particles with a particle size of 1000 μm or less, the laser diffraction/scattering method is preferably employed. To measure particles with a particle size exceeding 1000 μm, the sieve method is preferably employed.

The shape of the hydrogel particles is not specifically limited, and is preferably the shape of a body of revolution composed of a curved surface. The "body of revolution composed of a curved surface" herein means a shape defined by revolving a closed plane formed by a virtual axis and a continuous curve round on the virtual axis, and does not include shapes having flat surfaces such as triangular pyramids and cylinders. The shape of the hydrogel particles is more preferably spherical or oval from the viewpoint of aesthetic appearance.

Continuous Phase

The continuous phase is made of non-crosslinked hydrogel as an aqueous component, and includes a gel-forming agent and water.

The content of the continuous phase in the hydrogel particles is preferably 20-99 mass %, more preferably 25-85 mass %, and much more preferably 30-80 mass %, from the viewpoint of prevention of fracture in cleaning the hydrogel particles and incorporating the hydrogel particles in cosmetics or other products.

The "non-crosslinked hydrogel" herein means a product of gelation caused by the heat-reversibility of sol-gel. The dissolution temperature of the non-crosslinked hydrogel in water is preferably 75° C. or more in general and more preferably 75-90° C. The gelation temperature of the non-crosslinked hydrogel when cooled after dissolution in water is preferably 30-45° C.

The jelly strength of the non-crosslinked hydrogel is preferably 147 kPa (1500 g/cm$^2$) or less, and more preferably 19.6 kPa (200 g/cm$^2$) to 127 kPa (1300 g/cm$^2$) from the viewpoint of the feel of cosmetics or other products containing the hydrogel particles when used. The jelly strength can be obtained with a Nikkansuishiki method in the following manner. Specifically, first, a 1.5 mass % aqueous solution of a gel-forming agent is prepared, and is allowed to stand at 20° C. for 15 hours to obtain a gel product. Then, a load is applied to the gel using a Nikkansuishiki jelly strength measuring apparatus (manufactured by Kiya-seisakusho Co., Ltd.). The jelly strength is obtained as the maximum mass (g) per a unit surface area of 1 cm$^2$ when the gel withstands the load for 20 seconds at 20° C.

Gel-Forming Agent

Examples of the gel-forming agent include agar, carrageenan, and gelatin. Among these materials, agar is preferable. The gel-forming may be made of a single species or a plurality of species.

The content of the gel-forming agent in the continuous phase is 0.1 mass % or more, more preferably 0.3 mass % or more, much more preferably 0.4 mass % or more, and especially preferably 0.5 mass % or more, from the viewpoints of enhancing the feel of cosmetics or other products containing the hydrogel particles when used and preventing fracture in cleaning the hydrogel particles and incorporating the hydrogel particles in cosmetics or other products. The content of the gel-forming agent in the hydrogel particles is preferably 8.0 mass % or less, more preferably 7.0 mass % or less, much more preferably 6.0 mass % or less, and especially preferably 5.0 mass % or less, from the viewpoints of enhancing the feel of cosmetics or other products containing the hydrogel particles when used and preventing fracture in cleaning the hydrogel particles and incorporating the hydrogel particles in cosmetics or other products.

Dispersed Phase

The dispersed phase includes an oil component containing a solid fat and also includes a crystalline organic UV absorber.

The content of the dispersed phase in the hydrogel particles is preferably 1-70 mass %, more preferably 7.5-70 mass %, much more preferably 10-70 mass %, still much more preferably 15-60 mass %, and especially preferably 20-50 mass %, from the viewpoint of prevention of fracture in cleaning the hydrogel particles and incorporating the hydrogel particles in cosmetics or other products.

The volume-based average particle size of the dispersed phase is preferably 1/10 or less of the volume-based average particle size of the hydrogel particles. Specifically, the volume-based average particle size of the dispersed phase is preferably 0.01-100 μm, more preferably 0.5-50 μm, and much more preferably 0.5-20 μm, from the viewpoints of smooth spreadability over the skin of cosmetics or other products containing the hydrogel particles, prevention of leakage of the dispersed phase from the hydrogel particles, compatibility with the skin of cosmetics or other products containing the hydrogel particles. The volume-based average particle size of the dispersed phase in the state of a dispersion before formation of particles can be measured with a laser diffraction/scattering method using a laser diffraction/scattering particle size distribution analyzer (e.g., LA-920 manufactured by HORIBA, Ltd.).

Oil Component

The oil component includes a solid fat, but may be made only of a solid fat or may also include liquid oil. The "solid fat" herein is an oil component having a melting point of 35° C. or more. The "liquid oil" herein is an oil component having a melting point less than 35° C. The melting points of solid fat and liquid oil can be measured by differential scanning calorimetry (DSC).

The content of the oil component in the dispersed phase is preferably 30-85 mass %, more preferably 30-80 mass %, much more preferably 30-65 mass %, and especially preferably 40-60 mass %, from the viewpoint of enhancing the feel of cosmetics or other products containing the hydrogel particles when used. The total content of the oil component in the hydrogel particles is preferably 0.01-60 mass %, more preferably 3.0-50 mass %, much more preferably 5.0-40 mass %, and especially preferably 7.5-25 mass %, from the viewpoints of enhancing the feel of cosmetics or other products containing the hydrogel particles when used and preventing fracture in cleaning the hydrogel particles and incorporating the hydrogel particles in cosmetics or other products.

The melting point of the oil component is preferably 35° C. or more, more preferably 40-90° C., and much more preferably 40-80° C., from the viewpoint of preventing leakage of the oil component from the hydrogel particles during storage at high temperatures. The melting point of the oil component can also be measured by differential scanning calorimetry.

Solid Fat

The solid fat includes a solid fat having an organic value (OV) of 310 or more and an inorganic value (IV) of 130 or more on an organic conceptual diagram (hereinafter referred to as a "solid fat A").

The "organic conceptual diagram" herein is a diagram in which the degree of covalent bond of a compound is evaluated as an organic value (OV) and the degree of ionic bond is evaluated as an inorganic value (IV) and location of a compound is plotted as points (OV, IV) on a plane of rectangular coordinates with the abscissa used as an organic axis and the ordinate used as an inorganic axis. The organic value (OV) is obtained by multiplying the carbon number of the component by 20. The inorganic value (IV) is a cumulative sum of inorganic values provided to substituents included in the compound. With respect to inorganic values, see a table on page 13 in "Organic Conceptual Diagram—basis and application—" (Yoshio KODA, Sankyo Publishing, 1984).

The solid fat A has an organic value (OV) of 310 or more. The organic value (OV) of the solid fat A is preferably 330 or more, more preferably 350 or more, and much more preferably 400 or more. In addition, the organic value (OV) of the solid fat A is preferably 1000 or less and more preferably 800 or less. The solid fat A has an inorganic value (IV) of 130 or more. The inorganic value (IV) of the solid fat A is preferably 140 or more and more preferably 150 or more. In addition, the inorganic value (IV) of the solid fat A is preferably 800 or less, more preferably 700 or less, and much more preferably 500 or less.

As the inorganic value (IV)/organic value (OV)=IOB value, the solid fat A preferably has $0.20 \leq$ IOB value $\leq 1.10$ and more preferably $0.25 \leq$ IOB value $\leq 1.00$. As the JOB value× 10=HLB value, the solid fat A preferably has $2.03 \leq$ HLB value≤11.0 and more preferably 2.5≤HLB value≤10.0. The angle α formed by the organic axis and the line passing through the origin and points (OV, IV) of the solid fat A on the organic conceptual diagram is preferably 11°≤α≤48°, more preferably 13°≤α≤48°, and much more preferably 15°≤α≤47°.

Examples of the solid fat A include glycerin fatty acid esters, alkylene glycol fatty acid esters, and solid ceramide.

Examples of glycerin fatty acid esters include stearic acid monoglyceride (OV=420, IV=260, IOB value=0.62, HLB value=6.2), behenic acid monoglyceride (OV=500, IV=260, JOB value=0.52, HLB value=5.2), stearic acid monoglyceride succinate (OV=500, IV=380, IOB value=0.76, HLB value=7.6), stearic acid diglyceride (OV=780, IV=220, IOB value=0.28, HLB value=2.8), and behenic acid diglyceride (OV=860, IV=220, JOB value=0.26, HLB value=2.6).

Examples of alkylene glycol fatty acid esters include propylene glycol monostearate (OV=420, IV=160, IOB value=0.38, HLB value=3.8), and propylene glycol monobehenate (OV=500, IV=160, IOB value=0.32, HLB value=3.2).

Examples of solid ceramide include N-(2-hydroxy-3-hexadecyloxypropyl)-N-2-hydroxyethylhexadecanamide (OV=780, IV=355, IOB value=0.46, HLB value=4.6).

Among the above-mentioned types of the solid fat A, glycerin fatty acid esters and alkylene glycol fatty acid esters are preferable.

The solid fat A is preferably a compound expressed by the following general formula (1):

$$R_1COOCH_2(CHX)_nCH_2Y \quad (1)$$

(wherein n is a number of 1-4, X and Y independently represent H, OH, OCOR$_2$, or OCO(CH$_2$)$_2$COOH, and R$_1$ and R$_2$ independently represent linear saturated hydrocarbon groups each having 13-21 carbon atoms).

In the general formula (1), n is preferably 1-2, and more preferably 1 (one). In addition, X is more preferably H, OH, or OCOR$_2$. Further, Y is more preferably OH, OCOR$_2$, or OCO(CH$_2$)$_2$COOH.

The solid fat A may include a single species or a plurality of species.

The content of the solid fat A in the dispersed phase is preferably 1-85 mass %, more preferably 1-75 mass %, much more preferably 3-70 mass %, and still much more preferably 5-60 mass %, from the viewpoints of incorporating a large amount of a crystalline organic UV absorber with stability, preventing leakage of the oil component from the hydrogel particles, and easily spreading cosmetics or other projects containing the hydrogel particles over the skin. The total content of the solid fat A in the hydrogel particles is preferably 0.2-30 mass % and more preferably 1.0-20 mass %.

The melting point of the solid fat A is 35° C. or more, and is preferably 40-120° C. and more preferably 40° C.-80° C. from the viewpoint of preventing leakage of the oil component from the hydrogel particles.

The oil component may include only the solid fat A as a solid fat, or may include another solid fat in addition to the solid fat A as long as reduction of crystal precipitation by the high-concentration crystalline organic UV absorber is not inhibited. Examples of the solid fat included in addition to the solid fat A include solid paraffin and higher alcohol.

Liquid Oil

Examples of liquid oil include liquid skin-protecting agents, liquid UV absorbers, liquid oil products, and liquid perfume.

Examples of the liquid skin-protecting agents include: liquid fats and oils such as liquid paraffin, liquid ester oils, liquid higher alcohols, liquid squalanes, and liquid glycerides; and liquid ceramides such as cetyloxypropyl glyceryl methoxypropyl myristamide.

Examples of the liquid UV absorbers include p-aminobenzoic acid, methyl p-aminobenzoate, glyceryl p-aminobenzoate, p-dimethylaminoamyl bezoate, p-dimethylaminooctyl bezoate, ethylene glycol salicylate, phenyl salicylate, octyl salicylate, butylphenyl salicylate, homomentyl salicylate, octyl p-methoxy cinnamate, ethoxyethyl methoxy cinnamate, glyceryl monoethylhexanoyl dimethoxy cinnamate, hydroxymethoxy benzophenone, dihydroxydimethoxy benzophenone, and octyltriazone.

Examples of the liquid oil products include: liquid hydrocarbon oil; liquid vegetable oil; liquid fatty acids; liquid fats and oils such as liquid ethylene glycol difatty acid ester (in which a carbon number of fatty acid is 12-36 and which is a branched saturated or unsaturated hydrocarbon group), liquid dialkyl ester (in which the carbon number of fatty acid is 12-36 and which is a branched saturated or unsaturated hydrocarbon group); and liquid silicones.

The liquid oil may include a single species or a plurality of species.

The content of the liquid oil in the dispersed phase is preferably 0-75 mass %, more preferably 0-65 mass %, much more preferably 0-60 mass %, and still much more preferably 0-50 mass %, from the viewpoints of incorporating a large amount of the crystalline organic UV absorber having a low degree of solubility with stability and spreadability over the skin of cosmetics or other products containing the hydrogel particles. The total content of the liquid oil in the hydrogel particles is preferably 0-25 mass % and more preferably 0-20 mass %.

Crystalline Organic UV Absorber

The term "crystalline" herein means that a peak and a crystalline state can be observed by X-ray diffraction. The "organic UV absorber" herein means a compound having a property of absorbing ultraviolet radiation whose wavelength range is 280-400 nm, especially UVA whose wavelength range is 320-400 nm, and including no inorganic substances such as titanium and zinc. The presence/absence of the UV absorption property can be detected by using, for example, an SPF analyzer.

Examples of the crystalline organic UV absorber include diethylamino hydroxybenzoyl hexyl benzoate (OV=480, IV=325, IOB value=0.68, HLB value=6.77), dimethoxybenzylidene dioxoimidazolidine propionate octyl (OV=460, IV=462, IOB value=1.00, HLB value=10.04), and t-butyl methoxybenzoyl methane (OV=380, IV=180, IOB value=0.47, HLB value=4.74). The crystalline organic UV absorber may include a single species or a plurality of species.

The organic value (OV) of the crystalline organic UV absorber is preferably 310-800, more preferably 330-700, and much more preferably 350-600. The inorganic value (IV) of the crystalline organic UV absorber is preferably 130-700 and more preferably 150-600.

The crystalline organic UV absorber preferably has 0.30≤IOB value≤1.1 and more preferably 0.35≤IOB value≤1.00. The crystalline organic UV absorber preferably has 3.0≤HLB value≤11 and more preferably 3.5≤HLB value≤10.0. The crystalline organic UV absorber preferably has 16°≤α≤48°, more preferably 18°≤α≤48°, and much more preferably 21°≤α≤47° where α is an angle formed by an organic axis and a line passing through the origin and a point (OV, IV) on the organic conceptual diagram.

The organic value (OV) of the crystalline organic UV absorber is preferably within ±250, more preferably within ±200, much more preferably within ±150, and especially preferably within ±100, of the organic value (OV) of the solid fat A. The inorganic value (IV) of the crystalline organic UV absorber is preferably within ±350, more preferably within ±300, much more preferably within ±200, still much more preferably within ±150, and especially preferably within ±100, of the inorganic value (IV) of the solid fat A.

The content of the crystalline organic UV absorber in the dispersed phase is 15-70 mass %, and from the viewpoint of UV protection, preferably 20-70 mass % and more preferably 40-70 mass %. The content ratio of the crystalline organic UV absorber to the solid fat A in the dispersed phase (i.e., the content of the crystalline organic UV absorber in the dispersed phase/the content of the solid fat A in the dispersed phase) is preferably 0.1-50, more preferably 0.15-30, and more preferably 0.2-15. The total content of the crystalline organic UV absorber in the hydrogel particles is preferably 3-50 mass %, more preferably 5-40 mass %, and much more preferably 10-30 mass %, from the viewpoint of UV protection.

Optional Components

The continuous phase may include a water-soluble organic compound such as sugars, polyhydric alcohol, a water-soluble polymer compound, and water-soluble perfume described in Japanese Patent Publication No. 2000-126586, in addition to the gel-forming agent of non-crosslinked hydrogel and water.

Each of the continuous phase and the dispersed phase may include a component such as an emulsifying/dispersing agent, which will be described later, a coloring agent, or a preservative. Examples of the coloring agent include pigments and dyes. Examples of the pigments include inorganic pigments such as carbon black, iron red, and titanium oxide, and organic pigments such as tar dye. Examples of the dyes include oil-soluble dyes, vat dyes, and lake dyes. Examples of the preservatives include methyl p-hydroxybenzoate, isopropylmethylphenol, dehydroacetic acid, and salts thereof.

Each of the continuous phase and the dispersed phase may include components such as humectants, antiperspirants, antibacterial agents, bactericides, and powders, which are applicable to cosmetics, drugs, quasi drugs, and the like.

Method For Producing Hydrogel Particles

Now, a method for producing hydrogel particles according to this embodiment will be described.

Preparation of Oil-In-Water Dispersion

First, a solution mixture A is prepared by mixing an aqueous component of a gel-forming agent and ion-exchanged water as a continuous phase component solution and heating the solution mixture at its dissolution temperature or higher so that the component is sufficiently dissolved therein. On the other hand, a solution mixture B is prepared by mixing an oil component and a crystalline organic UV absorber as a dispersed phase component solution with heat so that the components are sufficiently dissolved therein. In this process, the dispersed phase component solution is prepared such that the content of the crystalline organic UV absorber in the dispersed phase of final hydrogel particles is 15-70 mass %.

Then, the continuous phase component solution (i.e., the solution mixture A) and the dispersed phase component solution (i.e., the solution mixture B) are mixed together at a gelation temperature or higher, thereby preparing an oil-in-water dispersion (mixture). In this process, the method for preparing the oil-in-water dispersion is not specifically limited, and any known technique using various types of agitators, dispersers, or the like may be employed. The oil-in-water dispersion is prepared such that the content of the crystalline organic UV absorber in the dispersed phase of final hydrogel particles is 15-70 mass %.

From the viewpoint of stability of the oil-in-water dispersion, before or after mixing of the continuous phase component solution and the dispersed phase component solution, an emulsifying/dispersing agent is preferably added to the continuous phase component solution and/or the dispersed phase component solution before the mixing or the solution mixture thereof after the mixing. Among these cases, it is more preferable to add the emulsifying/dispersing agent to the continuous phase component solution before the mixing.

Examples of the emulsifying/dispersing agent include polymer emulsifying/dispersing agents, nonionic surfactants, anionic surfactants, cationic surfactants, and amphoteric surfactants. A single species of the emulsifying/dispersing agent may be added, or a plurality of species of the emulsifying/dispersing agents may be added.

Among the above-listed emulsifying/dispersing agents, from the viewpoints of spreadability over the skin of cosmetics or other products containing the hydrogel particles and excellent handling in cleaning the hydrogel particles and incorporating the hydrogel particles in cosmetics or other products, the nonionic surfactant, the anionic surfactant, the cationic surfactant, a combination of the amphoteric surfactant and the polymer emulsifying/dispersing agent, or a combination of the nonionic surfactant and the polymer emulsifying/dispersing agent is preferably used, or the polymer emulsifying/dispersing agent is preferably used alone. In the case of using the polymer emulsifying/dispersing agent as the emulsifying/dispersing agent, addition of the surfactant can be reduced or eliminated, leading to reduction of greasiness by the surfactant when cosmetics or other products containing the hydrogel particles are applied onto the skin.

Examples of the polymer emulsifying/dispersing agent include acrylate-alkyl methacrylate copolymer, a complex synthesized from an amphoteric polymer compound and a higher fatty acid described in Japanese Patent Publication No. H07-100356, water-soluble amphiphilic polymer electrolytes described in Japanese Patent Publications Nos. H08-252447 and H09-141079, water-soluble crosslinked amphiphilic polymer electrolytes described in Japanese Patent Publications Nos. H09-141080 and H09-141081, acrylic acid copolymer described in Japanese Patent Publication No. H10-53625, polysaccharide derivatives described in Japanese Patent No. 3329689 and Japanese Patent Publications Nos. H10-330401 and H11-106401, synthetic polymer compounds such as polyvinylpyrrolidone, polyvinyl alcohol, and derivatives thereof, polyacrylamide, and ethylene oxide adducts of alkylphenol-formaldehyde condensation products, and natural polymer compounds such as guar gum, karaya gum, tragacanth gum, gum arabic, arabinogalactan, and casein.

Among the above polymer emulsifying/dispersing agents, from the viewpoint of reduction of greasiness of cosmetics or other products containing the hydrogel particles when applied onto the skin, an acrylate-alkyl methacrylate copolymer (e.g., Nikko Chemicals Co., Ltd., product name: PEMULEN), polyvinyl alcohol (e.g., Nippon Synthetic Chemical Industry Co., Ltd., product name: GOHSENOL), and a polysaccharide derivative described in Japanese Patent No. 3329689 are preferably used.

From the viewpoint of improvement of femulsifiability and dispersibility, a neutralized polymer emulsifying/dispersing agent may be added. Alternatively, a pH adjuster such as potassium hydroxide and sodium hydroxide may be added after the addition so as to neutralize the polymer emulsifying/dispersing agent. The pH after neutralization is preferably 4-8 and more preferably 6-7.

Examples of the anionic surfactants include sodium lauryl sulfate, sodium stearate, and polyoxyethylene lauryl ether sodium phosphate.

Examples of the cationic surfactants include lauryl trimethyl ammonium chloride, stearylamine acetate, and stearylamine acid.

From the viewpoint of prevention of leakage of the oil component from the final hydrogel particles, the nonionic surfactant having an HLB value of 10 or less is preferably used, the nonionic surfactant having an HLB value of 8 or less is more preferably used, the nonionic surfactant having an HLB value of 5 or less is much more preferably used, and the nonionic surfactant having an HLB value of 3 or less is especially preferably used. The HLB value can be determined based on a formula described in "Techniques of Emulsification and Solubilization" published by Kougakutosho Ltd. (May 20, 1984), pp. 8-12.

Among the nonionic surfactants mentioned above, from the viewpoint of less skin irritation cased by cosmetics or other products containing the final hydrogel particles, sorbitan fatty acid esters, polyoxyethylene sorbitan fatty acid esters, and polyoxyethylene sorbitol fatty acid esters are preferably used, and sorbitan monostearate is more preferably used. From the viewpoint of prevention of leakage of the oil component from the final hydrogel particles, the nonionic surfactant having a melting point of 35° C. or more is preferably used, the nonionic surfactant having a melting point of 40-90° C. is more preferably used, the nonionic surfactant having a melting point of 50-90° C. is much more preferably used, and the nonionic surfactant having a melting point of 60-80° C. is especially preferably used.

Examples of the amphoteric surfactants include alkydimethylaminoacetic acid betaine and lecithin.

Particle Formation of Oil-In-Water Dispersion

Then, after preparation of the oil-in-water dispersion, hydrogel particles are produced from the oil-in-water dispersion with a commonly-employed dropping, spraying, or stirring technique. From the viewpoint of prevention of leakage of the oil component from the hydrogel particles, the dropping technique and the spraying technique are more preferable than the stirring technique.

In the dropping technique, the oil-in-water dispersion is discharged through holes and, utilizing properties of the oil-in-water dispersion of changing into droplets due to its surface or interfacial tension, these droplets are solidified by cooling in a gas phase such as air or a liquid phase to form hydrogel particles. From the viewpoint of forming hydrogel particles with a uniform particle size, vibration is preferably applied to the oil-in-water dispersion which is being discharged through holes.

In the spraying technique, a spray nozzle is used to spray a dispersion therefrom, droplets are formed by utilizing the surface tension of the dispersion, and these droplets are solidified by cooling the droplets in a gas phase to form hydrogel particles.

In the stirring technique, the oil-in-water dispersion is added to a solution which has the property of not being substantially mixed with the oil-in-water dispersion and is adjusted at a gelation temperature or higher, then shearing force by stirring is applied to the resultant solution to change the oil-in-water dispersion into fine particles, and utilizing the property of changing into droplets by the interfacial tension, these droplets are solidified by cooling in the solution which is not substantially mixed with the oil-in-water dispersion, thereby producing hydrogel particles.

In each of these dropping, spraying, and stirring techniques, the temperature of the oil-in-water dispersion at discharge, spraying, or addition is preferably in the range from a gelation temperature to 100° C., both inclusive. From the viewpoint of easily producing aesthetic spherical particles, the oil-in-water dispersion is preferably at a temperature +10° C. higher than the gelation temperature or more and more preferably at a temperature +20° C. higher than the gelation temperature or more. The upper limit of the temperature of the oil-in-water dispersion is 100° C., which is the boiling point of water.

The size of the hydrogel particles obtained in the manner described above may be further reduced by pulverization or other processes, as necessary.

UV-Shielding Cosmetic Product

An UV-shielding cosmetic product having an UV-shielding property can be obtained by incorporating the hydrogel particles. In this case, the hydrogel particles are applicable to both w/o and o/w type cosmetic products. In particular, the o/w type cosmetic products are preferable.

The content of the hydrogel particles in an UV-shielding cosmetic product is preferably 5-80 mass %, more preferably 5-75 mass %, and much more preferably 5-50 mass %.

The UV absorbing effect of the UV-shielding cosmetic product can be enhanced by further including an organic UV absorber. The organic UV absorber is not specifically limited, and any one of an oil-soluble organic UV absorber or a water-soluble organic UV absorber may be used. For example, the organic UV absorber described in Japanese Patent Publication No. 2006-225311 may be used. Examples of the oil-soluble organic UV absorber include those based on benzoic acid, salicylic acid, cinnamic acid, benzophenone, benzoylmethane, triazine, and bonzotriazine.

The total content of the organic UV absorber in the UV-shielding cosmetic product is preferably 1-35 mass %, more preferably 5-30 mass %, and much more preferably 8-25 mass %, from the viewpoints of reduction of stickiness on the skin and the UV absorbing effect.

From the viewpoint of adjusting the feel, the UV-shielding cosmetic product may contain an oil product. Examples of the oil product include the oil product described in Japanese Patent Publication No. 2006-225311. Among the examples, ester oil and silicone oil are especially preferable in terms of improvement of the feel. The content of the oil product in the UV-shielding cosmetic product is preferably 0.1-15 mass % and more preferably 0.1-10 mass %.

The UV-shielding cosmetic product may include a surfactant (excluding a polymer emulsifying/dispersing agent) from the viewpoint of enhancement of stability of the cosmetic product. Examples of the surfactant include nonionic surfactants, anionic surfactants, cationic surfactants, and amphoteric surfactants as described above. The content of the surfactant (excluding the surfactant present in the hydrogel particles) in the UV-shielding cosmetic product is preferably 5 mass % or less, more preferably 3 mass % or less, and much more preferably 1 mass % or less, from the viewpoint of obtaining an excellent feeling on the skin.

In addition to the ingredients mentioned above, the UV-shielding cosmetic product may contain a polymer emulsifying/dispersing agent, a skin whitening agent, a bactericide, an antiperspirant, a humectant, a cooling agent, perfume, and/or a coloring agent, for example, as long as advantages of the present disclosure are not impaired.

Application of the above UV-shielding cosmetic product onto the skin can reduce stickiness or dryness of the skin, and moreover, these feels are sustained so that effective ingredients of, for example, the UV absorber can remain on the skin for a long time.

EXAMPLES

Test Evaluation 1

(Hydrogel Particles)

Hydrogel particles of Examples 1-9 and Comparative Examples 1-5 were produced in the following manner. Compositions of the hydrogel particles are also shown in Tables 1 and 2.

Example 1

A dispersed phase component solution including: stearic acid monoglyceride (Kao Corporation, product name: Reodol MS-60, OV=564, IV=244, IOB value=0.43, HLB value=4.3) as a solid fat of an oil component; and diethylamino hydroxybenzoyl hexyl benzoate (BASF Japan Ltd., product name: Uvinul Aplus, OV=480, IV=325, IOB value=0.68, HLB value=6.77) as a crystalline organic UV absorber was prepared. In this preparation, the content of stearic acid monoglyceride and diethylamino hydroxybenzoyl hexyl benzoate in the final hydrogel particles were 13.5 mass % and 13.5 mass %, respectively. The contents of stearic acid monoglyceride and diethylamino hydroxybenzoyl hexyl benzoate in the dispersed phase component solution were 50 mass % and 50 mass %, respectively. That is, the content ratio of the crystalline organic UV absorber to the solid fat was 1 (one). Reodol MS-60 produced by Kao Corporation is a solid fat containing stearic acid monoglyceride as a main component.

A continuous phase component solution including: agar (Ina Food Industry Co., Ltd., product name: AX-200) as a gel-forming agent; acrylate-alkyl methacrylate copolymer (Nikko Chemicals Co., Ltd., product name: PEMULEN TR-2) and polyvinyl alcohol (Nippon Synthetic Chemical Industry Co., Ltd., product name: GOHSENOLE G-05) as emulsifying/dispersing agents; a 1N—NaOH aqueous solution (KISHIDA CHEMICAL Co., Ltd.) as a pH adjuster; and ion-exchanged water was prepared. In this preparation, the contents of the above components in the final hydrogel particles were as follows: agar was 2.0 mass %; acrylate-alkyl methacrylate copolymer was 0.1 mass %; polyvinyl alcohol was 0.5 mass %; the 1N—NaOH aqueous solution was 0.75 mass %; and the balance was ion-exchanged water.

The dispersed phase component solution and the continuous phase component solution were prepared in a total amount of 1000 g such that the mass ratio thereof was 27:73. Then, the dispersed phase component solution and the continuous phase component solution were melted by heating at 80° C. and 90° C., respectively. Thereafter, the dispersed phase component solution was added to the continuous phase component solution, and the resultant mixture was stirred with a homomixer (PRIMIX Corporation, product name: T. K. Robomix) at a rotation speed of 8000 rpm for one minute, thereby preparing an oil-in-water dispersion.

This oil-in-water dispersion was sprayed through a spray nozzle (IKEUCHI Co., Ltd., hollow cone spray nozzle K-010) at a flow rate of 12 kg/hr into a gas phase at 25° C. in a tank at a height of 3.4 m, with the temperature of the oil-in-water dispersion being kept at 80° C. Then, at the bottom of the tank, droplets of the oil-in-water dispersion formed by spraying and solidified by cooling were collected as hydrogel particles of Example 1.

Example 2

Hydrogel particles of Example 2 having the same composition as those of Example 1 except for using propylene glycol monostearate (Taiyo Kagaku Co., Ltd., product name: Sun Soft No. 25, CD, OV=420, IV=160, IOB value=0.38, HLB value=3.8) as the solid fat of the oil component, were formed.

Example 3

Hydrogel particles of Example 3 having the same composition as those of Example 1 except for using propylene glycol monobehenate (Riken Vitamin Co., Ltd., product name: Rikemal PB-100, OV=500, IV=160, IOB value=0.32, HLB value=3.2) as the solid fat of the oil component, were formed.

Example 4

Hydrogel particles of Example 4 having the same composition as those of Example 1 except for the following aspects were formed. The hydrogel particles of Example 4 used stearic acid monoglyceride succinate (Kao Corporation, product name: Step SS, OV=500, IV=380, IOB value=0.76, HLB value=7.6) together with stearic acid monoglyceride as the solid fat of the oil component in such a manner that the contents of stearic acid monoglyceride and stearic acid monoglyceride succinate in the final hydrogel particles were 10.5 mass % and 3.0 mass %, respectively.

The contents of stearic acid monoglyceride, stearic acid monoglyceride succinate, and diethylamino hydroxybenzoyl hexyl benzoate in the dispersed phase component solution were 38.9 mass %, 11.1 mass %, and 50 mass %, respectively. That is, the content ratio of the crystalline organic UV absorber to the solid fat was 1 (one).

Example 5

Hydrogel particles of Example 5 having the same composition as those of Example 1 except for the following aspects were formed. The hydrogel particles of Example 5 used stearic acid monoglyceride as the solid fat of the oil component and also used octyl p-methoxy cinnamate (BASF Japan Ltd., product name: Uvinul MC80) as liquid oil in such a manner that the contents of stearic acid monoglyceride and octyl p-methoxy cinnamate in the final hydrogel particles were 9.0 mass % and 4.5 mass %, respectively.

The contents of stearic acid monoglyceride, octyl p-methoxy cinnamate, and diethylamino hydroxybenzoyl hexyl benzoate in the dispersed phase component solution were 33.3 mass %, 16.7 mass %, and 50 mass %, respectively. That is, the content ratio of the crystalline organic UV absorber to the solid fat was 1.5.

Example 6

Hydrogel particles of Example 6 having the same composition as those of Example 1 except that the content of stearic acid monoglyceride and diethylamino hydroxybenzoyl hexyl benzoate in the final hydrogel particles were 10.8 mass % and 16.2 mass %, respectively, were formed. The contents of stearic acid monoglyceride and diethylamino hydroxybenzoyl hexyl benzoate in the dispersed phase component solution were 40 mass % and 60 mass %, respectively. That is, the content ratio of the crystalline organic UV absorber to the solid fat was 1.5.

Comparative Example 1

Hydrogel particles of Comparative Example 1 having the same composition as those of Example 1 except for using behenyl alcohol (Kao Corporation, product name: Kalcol 220-80, OV=440, IV=100, IOB value=0.23, HLB value=2.3) as a solid fat, were formed.

Comparative Example 2

Hydrogel particles of Comparative Example 2 having the same composition as those of Example 1 except for the following aspects were formed. The hydrogel particles of Comparative Example 2 used lauric acid monoglyceride (Taiyo Kagaku Co., Ltd., product name: Sun Soft No. 750, OV=300, IV=260, IOB value=0.87, HLB value=8.7) as a solid fat in such a manner that the contents of lauric acid monoglyceride and diethylamino hydroxybenzoyl hexyl benzoate in the final hydrogel particles were 21.6 mass % and 5.4 mass %, respectively.

The contents of lauric acid monoglyceride and diethylamino hydroxybenzoyl hexyl benzoate in the dispersed phase component solution were 80 mass % and 20 mass %, respectively. That is, the content ratio of the crystalline organic UV absorber to the solid fat was 0.25.

Comparative Example 3

Hydrogel particles of Comparative Example 3 having the same composition as those of Comparative Example 2 except for using ethylene glycol distearate (TOHO Chemical Industry Co., Ltd., product name: Pegnol EDS, OV=760, IV=120, IOB value=0.16, HLB value=1.6) as a solid fat, were formed.

Comparative Example 4

Hydrogel particles of Comparative Example 4 having the same composition as those of Example 1 except that the contents of stearic acid monoglyceride and diethylamino hydroxybenzoyl hexyl benzoate in the final hydrogel particles were 5.4 mass % and 21.6 mass %, respectively, were formed. The contents of stearic acid monoglyceride and diethylamino hydroxybenzoyl hexyl benzoate in the dispersed phase component solution were 20 mass % and 80 mass %, respectively. That is, the content ratio of the crystalline organic UV absorber to the solid fat was 4.

TABLE 1

| | | | | Example | | | | |
|---|---|---|---|---|---|---|---|---|
| | | | | 1 | 2 | 3 | 4 | 5 |
| Composition of hydrogel particles mass % | Dispersed phase | solid fat | stearic acid monoglyceride Kao Corporation/Reodol MS-60 OV = 564, IV = 244, IOB value = 0.43, HLB value = 4.3 | 13.5 | | | 10.5 | 9.0 |
| | | | propylene glycol monostearate Taiyo Kagaku Co., Ltd./Sun Soft No. 25CD OV = 420, IV = 160, IOB value = 0.38, HLB value = 3.8 | | 13.5 | | | |
| | | | propylene glycol monobehenate Riken Vitamin Co., Ltd./Rikemal PB-100 OV = 500, IV = 160, IOB value = 0.32, HLB value = 3.2 | | | 13.5 | | |
| | | | stearic acid monoglyceride succinate Kao Corporation/Step SS OV = 500, IV = 380, IOB value = 0.76, HLB value = 7.6 | | | | 3.0 | |
| | | | behenyl alcohol Kao Corporation/KALCOL220-80 OV = 440, IV = 100, IOB value = 0.23, HLB value = 2.3 | | | | | |
| | | | lauric acid monoglyceride Taiyo Kagaku Co., Ltd./Sun Soft No. 750 OV = 300, IV = 260, IOB value = 0.87, HLB value = 8.7 | | | | | |
| | | | ethylene glycol distearate TOHO Chemical Industry Co., Ltd./Pegnol EDS OV = 760, IV = 120, IOB value = 0.16, HLB value = 1.6 | | | | | |
| | | liquid oil | octyl p-methoxy cinnamate BASF Japan Ltd./Uvinul MC80 | | | | | 4.5 |
| | | crystalline organic UV absorber | diethylamino hydroxybenzoyl hexyl benzoate BASF Japan Ltd./Uvinul Aplus OV = 480, IV = 325, IOB value = 0.68, HLB value = 6.77 | 13.5 | 13.5 | 13.5 | 13.5 | 13.5 |
| | Continuous phase | gel-forming agent | agar Ina Food Industry Co., Ltd./AX-200 | 2.0 | 2.0 | 2.0 | 2.0 | 2.0 |
| | | emulsifying/ dispersing agent | acrylate-alkyl methacrylate copolymer Nikko Chemicals Co., Ltd./PEMULEN TR-2 | 0.1 | 0.1 | 0.1 | 0.1 | 0.1 |
| | | | polyvinyl alcohol The Nippon Synthetic Chemical Industry Co., Ltd./GOHSENOLE G-05 | 0.5 | 0.5 | 0.5 | 0.5 | 0.5 |

TABLE 1-continued

| | | | | | | | | |
|---|---|---|---|---|---|---|---|---|
| | | pH adjuster | 1N NaOH KISHIDA CHEMICAL Co., Ltd. | 0.75 | 0.75 | 0.75 | 0.75 | 0.75 |
| | | | ion-exchanged water | balance | balance | balance | balance | balance |
| | | Content of crystalline organic UV absorber in dispersed phase (mass %) | | 50 | 50 | 50 | 50 | 50 |
| | | Volume-based average particle size of hydrogel particles (μm) | | 150 | 150 | 150 | 150 | 150 |
| Storage stability evaluation | | Presence of crystal precipitation after 2-week storage at room temperature | | No | No | No | No | No |
| | | Presence of crystal precipitation after 2-week storage in 5° C. atmosphere | | No | No | No | — | — |
| | | Presence of crystal precipitation after 2-week storage in 40° C. atmosphere | | No | No | No | — | — |

| | | | | Example | Comparative Example | | | |
|---|---|---|---|---|---|---|---|---|
| | | | | 6 | 1 | 2 | 3 | 4 |
| Composition of hydrogel particles mass % | Dispersed phase | solid fat | stearic acid monoglyceride Kao Corporation/Reodol MS-60 OV = 564, IV = 244, IOB value = 0.43, HLB value = 4.3 | 10.8 | | | | 5.4 |
| | | | propylene glycol monostearate Taiyo Kagaku Co., Ltd./Sun Soft No. 25CD OV = 420, IV = 160, IOB value = 0.38, HLB value = 3.8 | | | | | |
| | | | propylene glycol monobehenate Riken Vitamin Co., Ltd./Rikemal PB-100 OV = 500, IV = 160, IOB value = 0.32, HLB value = 3.2 | | | | | |
| | | | stearic acid monoglyceride succinate Kao Corporation/Step SS OV = 500, IV = 380, IOB value = 0.76, HLB value = 7.6 | | | | | |
| | | | behenyl alcohol Kao Corporation/KALCOL220-80 OV = 440, IV = 100, IOB value = 0.23, HLB value = 2.3 | | 13.5 | | | |
| | | | lauric acid monoglyceride Taiyo Kagaku Co., Ltd./Sun Soft No. 750 OV = 300, IV = 260, IOB value = 0.87, HLB value = 8.7 | | | 21.6 | | |
| | | | ethylene glycol distearate TOHO Chemical Industry Co., Ltd./Pegnol EDS OV = 760, IV = 120, IOB value = 0.16, HLB value = 1.6 | | | | 21.6 | |
| | | liquid oil | octyl p-methoxy cinnamate BASF Japan Ltd./Uvinul MC80 | | | | | |
| | | crystalline organic UV absorber | diethylamino hydroxybenzoyl hexyl benzoate BASF Japan Ltd./Uvinul Aplus OV = 480, IV = 325, IOB value = 0.68, HLB value = 6.77 | 16.2 | 13.5 | 5.4 | 5.4 | 21.6 |
| | Continuous phase | gel-forming agent | agar Ina Food Industry Co., Ltd./AX-200 | 2.0 | 2.0 | 2.0 | 2.0 | 2.0 |
| | | emulsifying/ dispersing agent | acrylate-alkyl methacrylate copolymer Nikko Chemicals Co., Ltd./PEMULEN TR-2 | 0.1 | 0.1 | 0.1 | 0.1 | 0.1 |
| | | | polyvinyl alcohol The Nippon Synthetic Chemical Industry Co., Ltd./GOHSENOLE G-05 | 0.5 | 0.5 | 0.5 | 0.5 | 0.5 |
| | | pH adjuster | 1N NaOH KISHIDA CHEMICAL Co., Ltd. | 0.75 | 0.75 | 0.75 | 0.75 | 0.75 |
| | | | ion-exchanged water | balance | balance | balance | balance | balance |
| | | Content of crystalline organic UV absorber in dispersed phase (mass %) | | 60 | 50 | 20 | 20 | 80 |
| | | Volume-based average particle size of hydrogel particles (μm) | | 176 | 150 | 150 | 150 | 161 |
| Storage stability evaluation | | Presence of crystal precipitation after 2-week storage at room temperature | | No | Yes | Yes | Yes | Yes |
| | | Presence of crystal precipitation after 2-week storage in 5° C. atmosphere | | No | — | — | — | No |
| | | Presence of crystal precipitation after 2-week storage in 40° C. atmosphere | | No | Yes | — | — | No |

Example 7

Hydrogel particles of Example 7 having the same composition as those of Example 1 except for the following aspects were formed. The hydrogel particles of Example 7 used dimethoxybenzylidene dioxoimidazolidine propionate octyl (Ajinomoto Co., Inc., product name: Soft Shade DH, OV=460, IV=462, IOB value=1.00, HLB value=10.04) as a crystalline organic UV absorber in such a manner that the contents of stearic acid monoglyceride and dimethoxybenzylidene dioxoimidazolidine propionate octyl in the final hydrogel particles were 21.6 mass % and 5.4 mass %, respectively.

The contents of stearic acid monoglyceride and dimethoxybenzylidene dioxoimidazolidine propionate octyl in the dispersed phase component solution were 80 mass % and 20 mass %, respectively. That is, the content ratio of the crystalline organic UV absorber to the solid fat was 0.25.

Example 8

Hydrogel particles of Example 8 having the same composition as those of Example 6 except for using propylene glycol monostearate as a solid fat, were formed.

Example 9

Hydrogel particles of Example 9 having the same composition as those of Example 6 except for using propylene glycol monobehenate as a solid fat, were formed.

Comparative Example 5

Hydrogel particles of Comparative Example 5 having the same composition as those of Example 7 except for using lauric acid monoglyceride as a solid fat, were formed.

Reference Example

For preparation, behenyl alcohol is used as a solid fat, and the contents of behenyl alcohol and dimethoxybenzylidene dioxoimidazolidine propionate octyl in the final hydrogel particles were 21.6 mass % and 5.4 mass %, respectively. However, these components were not dissolved in each other. Thus, no dispersed phase component solution was prepared.

TABLE 2

| | | | | Example | | | Comparative Example |
| --- | --- | --- | --- | --- | --- | --- | --- |
| | | | | 7 | 8 | 9 | 5 |
| Composition of hydrogel particles mass % | Dispersed phase | solid fat | stearic acid monoglyceride Kao Corporation/Reodol MS-60 OV = 564, IV = 244, IOB value = 0.43, HLB value = 4.3 | 21.6 | | | |
| | | | propylene glycol monostearate Taiyo Kagaku Co., Ltd./Sun Soft No. 25CD OV = 420, IV = 160, IOB value = 0.38, HLB value = 3.8 | | 21.6 | | |
| | | | propylene glycol monobehenate Riken Vitamin Co., Ltd./Rikemal PB-100 OV = 500, IV = 160, IOB value = 0.32, HLB value = 3.2 | | | 21.6 | |
| | | | lauric acid monoglyceride Taiyo Kagaku Co., Ltd./Sun Soft No. 750 OV = 300, IV = 260, IOB value = 0.87, HLB value = 8.7 | | | | 21.6 |
| | | crystalline organic UV absorber | dimethoxybenzylidene dioxoimidazolidine propionate octyl Ajinomoto Co., Inc./Soft Shade DH OV = 460, IV = 462, IOB value = 1.00, HLB value = 10.04 | 5.4 | 5.4 | 5.4 | 5.4 |
| | Continuous phase | gel-forming agent | agar Ina Food Industry Co., Ltd./AX-200 | 2.0 | 2.0 | 2.0 | 2.0 |
| | | emulsifying/ dispersing agent | acrylate-alkyl methacrylate copolymer Nikko Chemicals Co., Ltd./PEMULEN TR-2 | 0.1 | 0.1 | 0.1 | 0.1 |
| | | | polyvinyl alcohol The Nippon Synthetic Chemical Industry Co., Ltd./GOHSENOLE G-05 | 0.5 | 0.5 | 0.5 | 0.5 |
| | | pH adjuster | 1N NaOH KISHIDA CHEMICAL Co., Ltd. | 0.75 | 0.75 | 0.75 | 0.75 |
| | | | ion-exchanged water | balance | balance | balance | balance |
| | Content of crystalline organic UV absorber in dispersed phase (mass %) | | | 20 | 20 | 20 | 20 |
| | Volume-based average particle size of hydrogel particles (μm) | | | 150 | 150 | 150 | 150 |
| Storage stability evaluation | | | Presence of crystal precipitation after 2-week storage at room temperature | No | No | No | Yes |
| | | | Presence of crystal precipitation after 2-week storage in 5° C. atmosphere | — | No | No | — |
| | | | Presence of crystal precipitation after 2-week storage in 40° C. atmosphere | — | No | No | — |

Test Evaluation Method

Volume-Based Average Particle Size

Median particle sizes of the hydrogel particles of Examples 1-9 and Comparative Examples 1-5 were measured with a laser diffraction/scattering particle size distribution analyzer (HORIBA, Ltd., product number: LA-920), and the obtained median particle sizes were used as volume-based average particle sizes of the hydrogel particles.

Storage Stability Evaluation

For the hydrogel particles of each of Examples 1-9 and Comparative Examples 1-5, slurry having a composition in which the content of the hydrogel particles was 50 mass %, the content of phenoxyethanol (TOHO Chemical Industry Co., Ltd., product name: High-solve EPH) was 0.2 mass %, the content of ethanol was 8.31 mass %, and the content of purified water was 41.49 mass % as shown in Table 3 was prepared.

TABLE 3

| Slurry composition mass % | hydrogel particles | 50 |
|---|---|---|
| | phenoxyethanol TOHO Chemical Industry Co., Ltd./ High-solve EPH | 0.2 |
| | ethanol | 8.31 |
| | purified water | 41.49 |

After the slurry has been stored for 2 weeks at room temperature, the state of the dispersed phase in the hydrogel particles was observed with a CCD (KEYENCE, product name: DIGITAL MICROSCOPE VHX-500) to detect the presence/absence of crystal precipitation of the crystalline organic UV absorber. The state in which the crystalline organic UV absorber grew to be coarse needle crystal with a size of 50 μm or more in the dispersed phase is defined as the presence (Yes) of crystal precipitation, whereas the state in which no such growth was observed is defined as the absence (No) of crystal precipitation.

A test evaluation similar to the case of storage for 2 weeks in a 5° C. atmosphere was conducted on the hydrogel particles of Examples 1-3, 6, 8, and 9, and Comparative Example 4. A test evaluation similar to the case of storage for 2 weeks in a 40° C. atmosphere was conducted on the hydrogel particles of Examples 1-3, 6, 8, and 9, and Comparative Examples 1 and 4.

Test Evaluation Results

Test evaluation results are shown in Tables 1 and 2.

With respect to the volume-based average particle size, Examples 1-5 and 7-9 and Comparative Examples 1-3 and 5 were 150 μm, Example 6 was 176 μm, and Comparative Example 4 was 161 μm.

With respect to the storage stability evaluation at room temperature, Examples 1-9 showed the absence (No) of crystal precipitation, whereas Comparative Examples 1-5 showed the presence (Yes) of crystal precipitation.

With respect to the storage stability evaluation in a 5° C. atmosphere, Examples 1-3, 6, 8, and 9, and Comparative Example 4 showed the absence (No) of crystal precipitation.

With respect to the storage stability evaluation in a 40° C. atmosphere, Examples 1-3, 6, 8, and 9, and Comparative Example 4 showed the absence (No) of crystal precipitation, whereas Comparative Example 1 showed the presence (Yes) of crystal precipitation.

Test Evaluation 2

UV-Shielding Cosmetic Product

Example 10

For the hydrogel particles of Example 1, slurry with a composition in which the content of hydrogel particles was 50 mass %, the content of phenoxyethanol (TOHO Chemical Industry Co., Ltd., product name: High-solve EPH) was 0.2 mass %, the content of ethanol was 10.00 mass %, and the content of purified water was 39.8 mass %, was prepared. To examine applicability of this slurry to UV-shielding cosmetic products, cosmetic base materials described in Table 4 were added to prepare an UV-shielding cosmetic product of Example 10.

Specific composition was as follows: hydrogel particle slurry was 20 mass %; 2-ethylhexyl p-methoxy cinnamate (BASF Corporation, product name: Uvinul MC80) was 8.5 mass %; dimeticone (Shin-Etsu Chemical Co., Ltd., product name: Silicone KF-96A (10cs)) was 1.0 mass %; acrylic acid copolymer (Nikko Chemicals Co., Ltd., product name: Carbopol ETD2020) was 0.1 mass %; acrylate-alkyl methacrylate copolymer (Nikko Chemicals Co., Ltd., product name: PEMULEN TR-2) was 0.2 mass %; acrylate-alkyl methacrylate copolymer (Nikko Chemicals Co., Ltd., product name: PEMULEN TR-1) was 0.2 mass %; phenoxyethanol (TOHO Chemical Industry Co., Ltd., product name: High-solve EPH) was 0.4 mass %; liquid caustic potash (48%) was 0.36 mass %; ethanol was 10 mass %; and the balance was purified water.

Comparative Example 6

Cosmetic base materials described in Table 4 were mixed to prepare an UV-shielding cosmetic product of Comparative Example 6.

Specifically, in Comparative Example 6, the composition was as follows: 2-ethylhexyl p-methoxy cinnamate (BASF Corporation, product name: Uvinul MC80) was 8.5 mass %; dimeticone (Shin-Etsu Chemical Co., Ltd., product name: Silicone KF-96A (10cs)) was 1.0 mass %; diethylamino hydroxybenzoyl hexyl benzoate (BASF Corporation, product name: Uvinul Aplus) was 1.35 mass %; glyceryl stearte (Kao Corporation, product name: Reodol MS-60) was 1.35 mass %; acrylic acid copolymer (Nikko Chemicals Co., Ltd., product name: Carbopol ETD2020) was 0.1 mass %; acrylate-alkyl methacrylate copolymer (Nikko Chemicals Co., Ltd., product name: PEMULEN TR-2) was 0.2 mass %; acrylate-alkyl methacrylate copolymer (Nikko Chemicals Co., Ltd., product name: PEMULEN TR-1) was 0.2 mass %; phenoxyethanol (TOHO Chemical Industry Co., Ltd., product name: High-solve EPH) was 0.4 mass %; liquid caustic potash (48%) was 0.36 mass %; ethanol was 10 mass %; and the balance was purified water.

TABLE 4

| | Example 10 | Comparative Example 6 |
|---|---|---|
| hydrogel particle slurry | 20 | 0 |
| 2-ethylhexyl p-methoxy cinnamate | | |

TABLE 4-continued

| | Example 10 | Comparative Example 6 |
|---|---|---|
| BASF Corporation product name: Uvinul MC80 | 8.5 | 8.5 |
| dimeticone Shin-Etsu Chemical Co., Ltd. product name: Silicone KF-96A (10cs) | 1.0 | 1.0 |
| diethylamino hydroxybenzoyl hexyl benzoate BASF Corporation product name: Uvinul Aplus | | 1.35 |
| glyceryl stearte Kao Corporation, product name: Reodol MS-60 | | 1.35 |
| acrylic acid copolymer Nikko Chemicals Co., Ltd. product name. Carbopol ETD2020 | 0.1 | 0.1 |
| acrylate-alkyl methacrylate copolymer Nikko Chemicals Co., Ltd. product name: PEMULEN TR-2 | 0.2 | 0.2 |
| acrylate-alkyl methacrylate copolymer Nikko Chemicals Co., Ltd. product name: PEMULEN TR-1 | 0.2 | 0.2 |
| phenoxyethanol TOHO Chemical Industry Co., Ltd. product name: High-solve EPH | 0.4 | 0.4 |
| liquid caustic potash (48%) | 0.36 | 0.36 |
| ethanol | 10 | 10 |
| purified water | balance | balance |
| Feeling | 4.3 | 4.3 |
| Storage stability (50° C., one month) | A | C |
| Separation confirmation test (200-mL beaker, rotation speed: 10 rpm, stirring for 60 minutes) | A | C |

Test Evaluation Method

Actual Use Test

UV-shielding cosmetic products including the hydrogel particles of Example 10 and Comparative Example 6 were applied forearms of three expert panelists, and an actual use test on moistness of the skin was conducted. Then, the average scores of the three panelists were obtained based on the following criteria.

Criteria

Score 5: moist
Score 4: slightly moist
Score 3: neither
Score 2: slightly not moist
Score 1: not moist Storage Stability Test The UV-shielding cosmetic products including the hydrogel particles of Example 10 and Comparative Example 6 were allowed to stand and, after one-month storage in a 50° C. atmosphere, the presence/absence of separation was visually inspected, thus performing evaluation based on the following criteria.

Separation Inspection Test

In this test, 200 mL of each of the UV-shielding cosmetic products including the hydrogel particles of Example 10 and Comparative Example 6 was placed in a 200-mL beaker, and after 60-minutes stirring with an agitator at a rotation speed of 10 rpm, the presence/absence of separation was visually inspected, thus performing evaluation based on the following criteria.

A: no separation
B: slightly separated
C: separated

Test Evaluation Results

Table 4 shows test evaluation results.
With respect to the average score of the feel in the actual use test, Example 10 showed 4.3 and Comparative Example 6 showed 4.3.
With respect to the storage stability after one month at 50° C., Example 10 showed A and Comparative Example 6 showed C.
With respect to the presence/absence in the separation inspection test, Example 10 showed A and Comparative Example 6 showed C.

INDUSTRIAL APPLICABILITY

The present disclosure is useful for hydrogel particles and methods for producing hydrogel particles.

The invention claimed is:

1. Hydrogel particles, comprising:
   a continuous phase of non-crosslinked hydrogel; and
   a dispersed phase dispersed in the continuous phase, wherein
   the dispersed phase comprises a crystalline organic UV absorber and a solid fat having an organic value of 310-1000 and an inorganic value of 130-800 on an organic conceptual diagram, and
   a content of the crystalline organic UV absorber in the dispersed phase is 15-70 mass %,
   wherein the solid fat is present in an amount that reduces crystal precipitation of the crystalline organic UV absorber.

2. The hydrogel particles of claim 1, wherein a ratio (IV)/(OV) of the inorganic value (IV) to the organic value (OV) of the solid fat on the organic conceptual diagram is 0.20-1.10.

3. The hydrogel particles of claim 1, wherein the crystalline organic UV absorber has an organic value of 310-800 and an inorganic value of 130-700 on the organic conceptual diagram.

4. The hydrogel particles of claim 1, wherein a ratio (IV)/(OV) of the inorganic value (IV) to the organic value (OV) of the crystalline organic UV absorber on the organic conceptual diagram is 0.30-1.1.

5. The hydrogel particles of claim 1, wherein the solid fat is a compound expressed by general formula (1):

$$R_1COOCH_2(CHX)_nCH_2Y \quad (1)$$

wherein n is a number of 1-4, X and Y are independently H, OH, $OCOR_2$, or $OCO(CH_2)_2COOH$, and $R_1$ and $R_2$ independently represent linear saturated hydrocarbon groups each having 13-21 carbon atoms.

6. The hydrogel particles of claim 1, wherein the solid fat comprises at least one of a glycerin fatty acid ester or an alkylene glycol fatty acid ester.

7. The hydrogel particles of claim 1, wherein a total content of the solid fat in the hydrogel particles is 0.2-30 mass %.

8. The hydrogel particles of claim 1, wherein a total content of the crystalline organic UV absorber in the hydrogel particles is 3-50 mass %.

9. The hydrogel particles of claim 1, wherein a total content of an oil component in the hydrogel particles is 0.01-60 mass %.

10. The hydrogel particles of claim 1, wherein a content of the continuous phase in the hydrogel particles is 20-99 mass %.

11. The hydrogel particles of claim 1, wherein the continuous phase comprises a gel-forming agent and water.

12. The hydrogel particles of claim 1, wherein a content of the dispersed phase in the hydrogel particles is 1-70 mass %.

13. The hydrogel particles of claim 1, wherein a content of the solid fat in the dispersed phase is 1-85 mass %.

14. The hydrogel particles of claim 1, wherein a content ratio of the crystalline organic UV absorber to the solid fat in the dispersed phase (a content of the crystalline organic UV absorber in the dispersed phase/a content of the solid fat in the dispersed phase) is 0.1-50.

15. The hydrogel particles of claim 1, wherein the crystalline organic UV absorber is diethylamino hydroxybenzoyl hexyl benzoate, dimethoxybenzylidene dioxoimidazolidine propionate octyl, or t-butyl methoxybenzoyl methane.

16. An UV-shielding cosmetic product comprising the hydrogel particles of claim 1.

17. The UV-shielding cosmetic product of claim 16, wherein a content of the hydrogel particles in an UV-shielding cosmetic product is 5-80 mass %.

18. A method for producing hydrogel particles in which a dispersed phase comprising a crystalline organic UV absorber and a solid fat having an organic value of 310-1000 and an inorganic value of 130-800 on an organic conceptual diagram is dispersed in a continuous phase of non-crosslinked hydrogel comprising a gel-forming agent and water, by dropping, spraying, or stirring a mixture comprising the crystalline organic UV absorber, the solid fat, the gel-forming agent, and the water, wherein the mixture is prepared such that a content of the crystalline organic UV absorber in the dispersed phase in the hydrogel particles is 15-70 mass %.

19. The method of claim 18, wherein the mixture is prepared by mixing at a gelation temperature of the gel-forming agent or higher.

20. The method of claim 19, wherein the mixture is prepared by mixing a mixture A comprising the gel-forming agent and water and a mixture B comprising the crystalline organic UV absorber and the solid fat at the gelation temperature of the gel-forming agent or higher.

21. The hydrogel particles of claim 1, wherein a content of the solid fat in the dispersed phase is 5-85 mass %, and a content ratio of the crystalline organic UV absorber to the solid fat in the dispersed phase (a content of the crystalline organic UV absorber in the dispersed phase/a content of the solid fat in the dispersed phase) is 0.2-15.

22. A method for reducing crystal precipitation of a crystalline organic UV absorber in hydrogel particles comprising a continuous phase of non-crosslinked hydrogel and a dispersed phase dispersed in the continuous phase, the dispersed phase comprising 15-70 mass % of the crystalline organic UV absorber, the method comprising including a solid fat having an organic value of 310-1000 and an inorganic value of 130-800 on an organic conceptual diagram in the dispersed phase.

23. The method of claim 22, wherein a content of the solid fat in the dispersed phase is 5-85 mass %, and a content ratio of the crystalline organic UV absorber to the solid fat in the dispersed phase (a content of the crystalline organic UV absorber in the dispersed phase/a content of the solid fat in the dispersed phase) is 0.2-15.

* * * * *